US008244366B2

(12) United States Patent
Chang et al.

(10) Patent No.: US 8,244,366 B2
(45) Date of Patent: Aug. 14, 2012

(54) COCHLEAR IMPLANT

(75) Inventors: Y. Jay Chang, Fullerton, CA (US); Dong Hyuk Lee, Gimpo-si (KR)

(73) Assignee: Material Solutions Technology Co., Ltd., Seongnam-si (KR)

( * ) Notice: Subject to any disclaimer, the term of this patent is extended or adjusted under 35 U.S.C. 154(b) by 778 days.

(21) Appl. No.: 12/097,751

(22) PCT Filed: Jun. 25, 2007

(86) PCT No.: PCT/KR2007/003071
§ 371 (c)(1),
(2), (4) Date: Aug. 22, 2008

(87) PCT Pub. No.: WO2008/010647
PCT Pub. Date: Jan. 24, 2008

(65) Prior Publication Data
US 2009/0005836 A1    Jan. 1, 2009

(30) Foreign Application Priority Data
Jul. 21, 2006   (KR) .................. 10-2006-0068626

(51) Int. Cl.
*A61F 11/04*    (2006.01)
(52) U.S. Cl. .............. 607/57; 607/1; 607/2; 607/55; 607/56; 607/115; 607/116; 607/118; 607/136; 607/137; 607/139

(58) Field of Classification Search .............. 607/1–2, 607/55–57, 115–116, 118, 136–137, 139
See application file for complete search history.

(56) References Cited

U.S. PATENT DOCUMENTS

| 5,095,904 A * | 3/1992 | Seligman et al. ............ 607/57 |
| 5,922,017 A | 7/1999 | Bredberg et al. |
| 6,487,453 B1 * | 11/2002 | Kuzma et al. ............... 607/137 |
| 2006/0122664 A1 * | 6/2006 | Sacha et al. ................ 607/57 |

FOREIGN PATENT DOCUMENTS
KR    20030046364    6/2003
* cited by examiner

*Primary Examiner* — Carl H Layno
*Assistant Examiner* — Deborah Malamud
(74) *Attorney, Agent, or Firm* — Hosoon Lee; Portland IP Law LLC

(57) ABSTRACT

There is provided a cochlear implant for improving the hearing ability of a patient suffered from hearing impairment comprising an internal receiving unit implanted into the body, which comprises a receiving part for receiving external signal, an active electrode and a reference electrode, characterized in that the active electrode is constructed with a single electrode wire having different thickness in at least two different regions. The active electrode of the internal receiving unit is inserted into a space formed at between the mastoid bone and the ear canal skin and end of the active electrode is inserted into the scala tympani of the cochlea and directly stimulates spiral ganglion. The cochlear implant provides easier implantation into the body and improved hearing ability at a lower cost.

9 Claims, 4 Drawing Sheets

[Fig. 1]
PRIOR ART
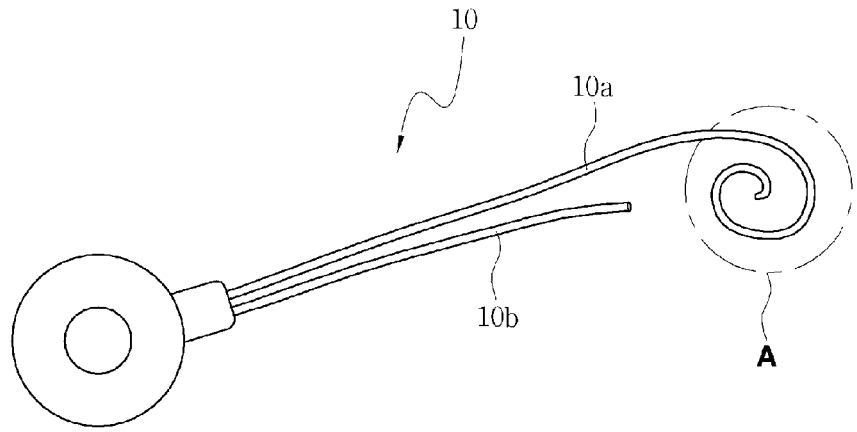
[Fig. 2]
PRIOR ART
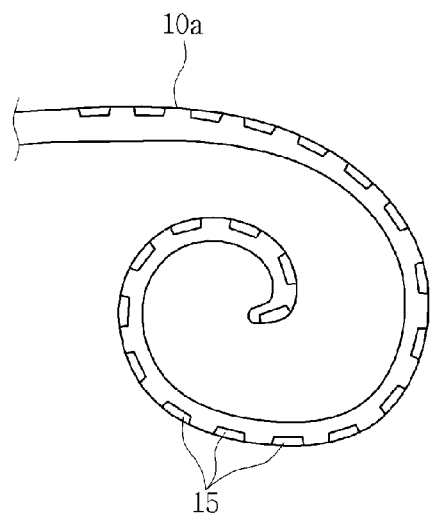
[Fig. 3]
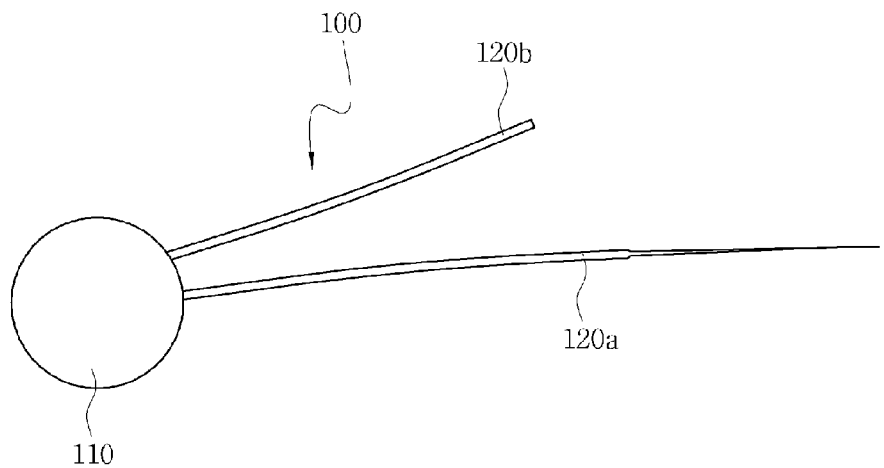

[Fig. 4]
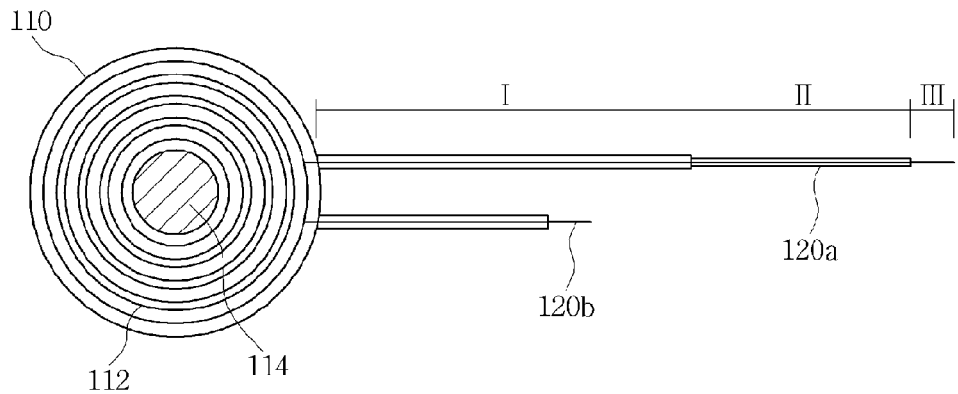
[Fig. 5]
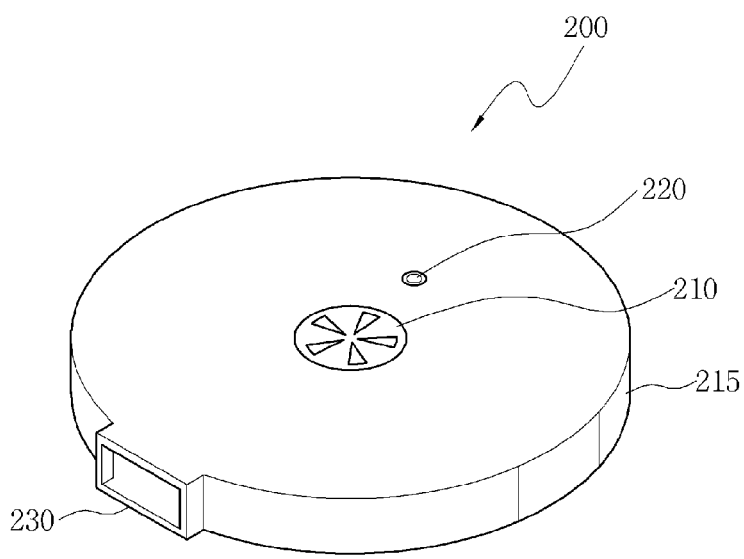
[Fig. 6]
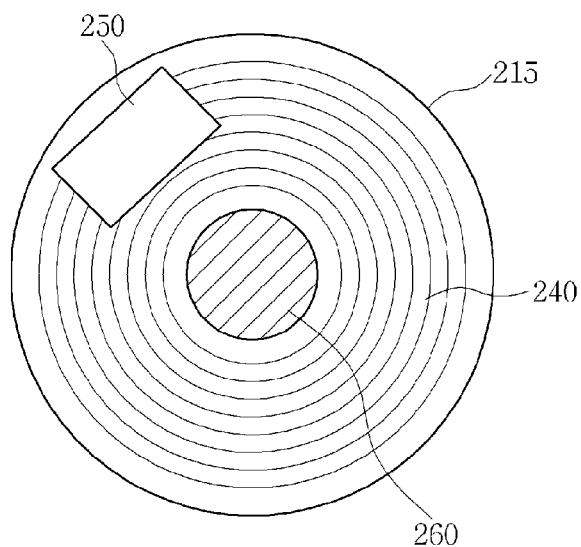

[Fig. 7]
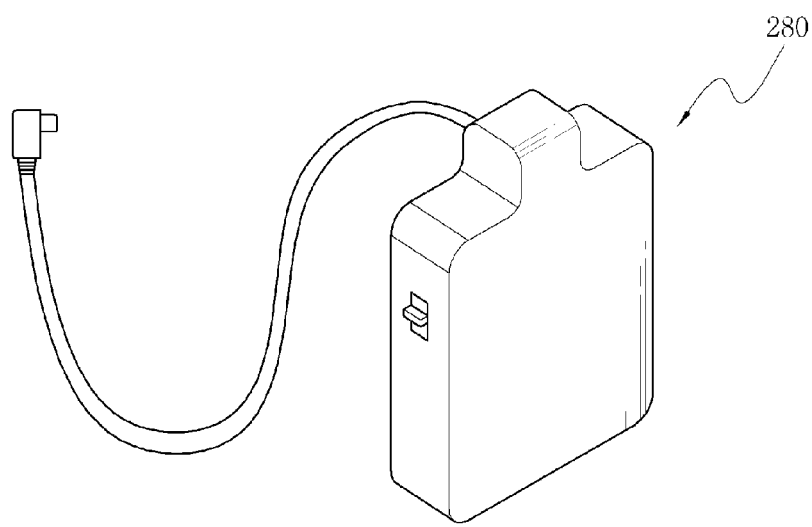
[Fig. 8]
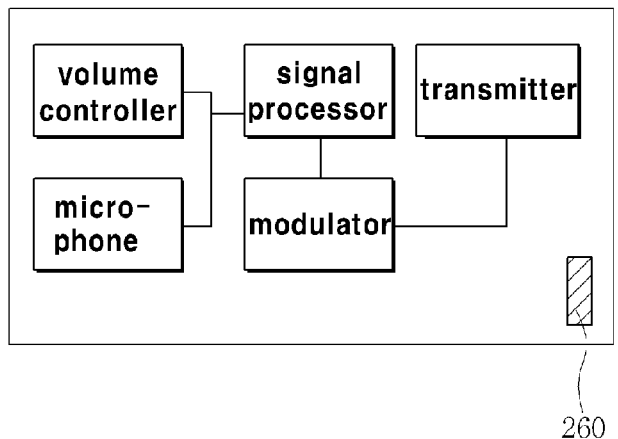
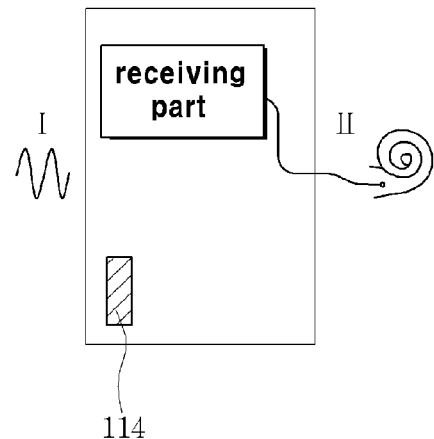

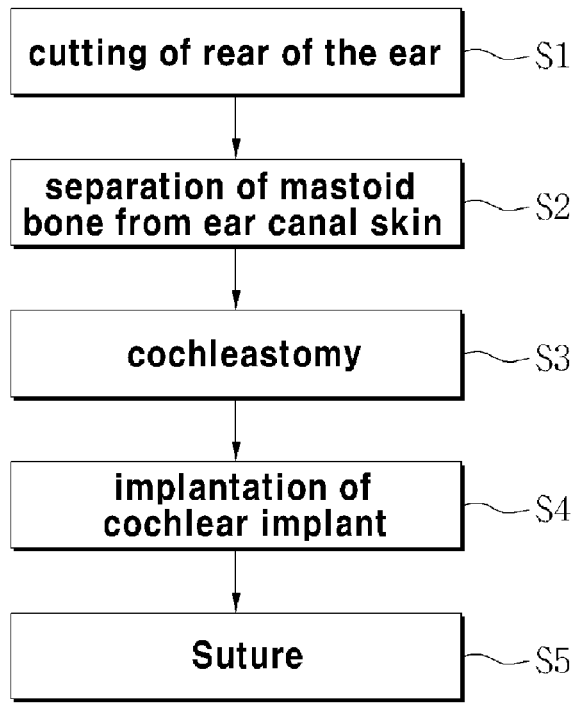
[Fig. 9]
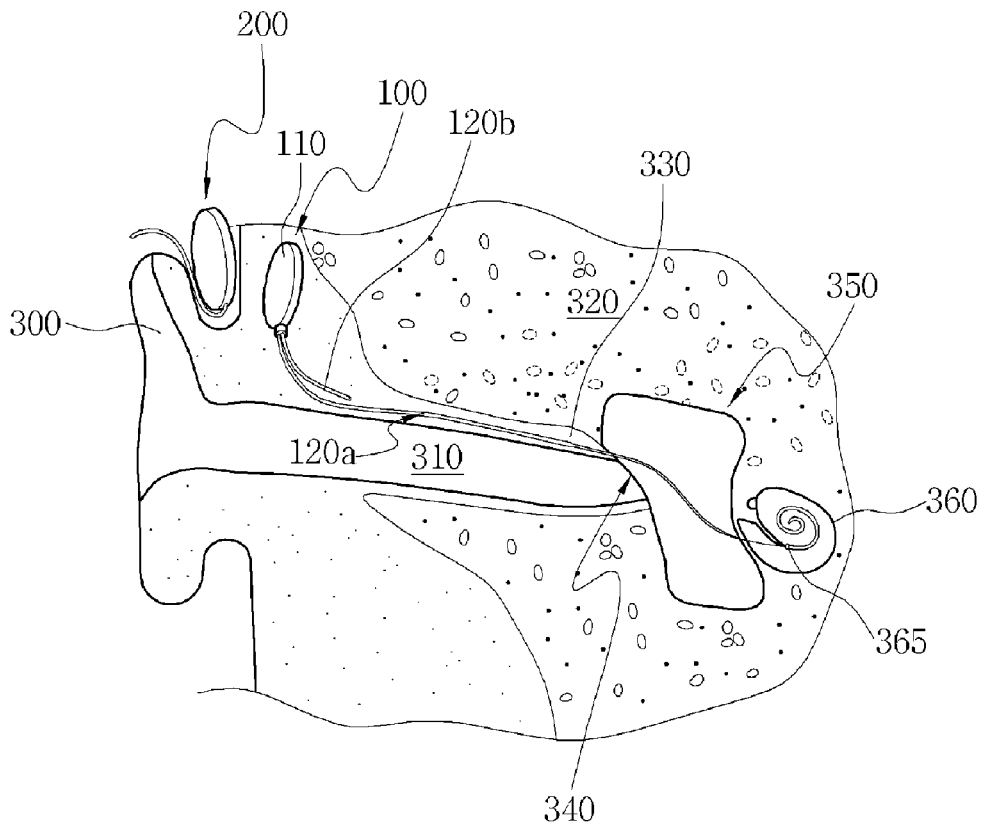
[Fig. 10]

COCHLEAR IMPLANT

TECHNICAL FIELD

The present invention relates to a cochlear implant, more particularly to a cochlear implant which can be easily implanted and provides improved hearing ability.

BACKGROUND ART

An ear is comprised of three basic parts an outer ear, a middle ear and an inner ear. Sound travels from the outer ear to an eardrum at the interface of the outer ear and then to the middle ear in the form of vibrating air waves. Then, it is transmitted to the oval window of the cochlea through the vibrations of the auditory ossicles. With the vibration of fluid in the cochlea, corti organ produces an electrical signal.

The vibration of the tectorial membrane leads to the generation of a receptor potential in the hair cells, which is transmitted to the spiral ganglion through dendrites. The signal from the spiral ganglion stimulates neurons of the auditory nerves and is finally transmitted to the cerebrum. Most hearing loss is due to poor function of the hair cell in the cochlea. In this case, the hearing loss can be alleviated by providing an artificial electrical stimulation, in replacement of the firing of hair cells. Cochlear implants have been developed based on the fact.

A cochlear implant is an electronic device surgically implanted into the body that provides a sense of sound to a person who is suffered from severely low hearing. The cochlear implant directly stimulates an auditory nerves inside the cochlea with electrical impulses. Cochlear implants provide good hearing ability to those who have severe hearing impairment in both ears and are not benefited by hearing aids. The cochlear implant is evaluated as the most successful nerve aiding device developed thus far.

Since approved by the United States Food and Drug Administration (FDA) in 1984, cochlear implants have been widespread. Recently, a multi-channel cochlear implant has been proposed. The multi-channel cochlear implant requires multiple electrodes in order to produce individual frequency signals, each of which is mapped to a particular location in the cochlea. Electrode signals that match the frequency requirements are transmitted individually to the dendrites below impaired hair cells.

FIG. 1 is a schematic view of the internal receiving unit (10) of the conventional cochlear implant having multiple electrodes. It comprises an active electrode (10a) and a reference electrode (10b), wherein end of the active electrode (A) is spirally shaped for convenient insertion into the cochlea. FIG. 2 shows an exploded view of the end of the active electrode (A). At the end of the active electrode (10a), multiple electrodes (15) are installed, each of which providing an electrical stimulation of a particular frequency to the specific area of the cochlea.

The cochlear implant comprising the multiple electrodes is as long as approximately 35 mm and may impair the hair cells while being inserted into the cochlea. Further, the spiral end of the electrode may cause damage to various organs such as the hair cells, dendrites or spiral ganglion when it touches the inner wall of the cochlea and may lead to a permanent hearing loss.

Patients with multi-channel cochlear implants show approximately 80% of sound recognition in the noiseless, silent environment. However, the level of recognition decreases in noisy place where many people are talking. Also, they have difficulty in enjoying music and, particularly, show significantly poor tonal sensibility.

Besides, the conventional multi-channel cochlear implants are suffered from various disadvantages such as expensive cost, very complicated surgery and risk of ins anitariness.

DISCLOSURE OF INVENTION

Technical Problem

An object of the present invention is to provide a new cochlear implant offering improved hearing ability.

Another object of the present invention is to provide a cochlear implant having a simpler construction and thus can be provided to the patients at a lower cost.

Yet another object of the present invention is to provide a cochlear implant that can be easily implanted and ensures safety with minimized risk during or following the surgery.

The objects and features of the present invention would be apparent from the detailed description.

Technical Solution

The cochlear implant of the present invention provides the patients suffered from severe sensorineural hearing impairment with improved hearing. The cochlear implant of the present invention would be helpful to the patients who are hardly or not benefited by hearing aids.

The cochlear implant of the present invention comprises an internal receiving unit which is implanted inside the body and receives a signal, and a sound processing unit which is positioned outside and produces the signal. It may further comprise a power supply unit comprising a battery pack or a charger for power supply.

Power is supplied through the power supplying unit. A microphone receives an analog sound and transmits it to the sound processing unit for the processing of the sound. Output of the signal processing unit is transmitted to the internal receiving unit through a coil. The user can control the strength of the sound to be transmitted by raising or lowering volume.

The signal is transmitted to the electrodes of the internal receiving unit implanted into the body and then to the cochlea through the electrode. The signal is finally delivered to the brain and the sound is recognized.

In the cochlear implant according to the present invention, the internal receiving unit is a receiving module implanted inside the body. It delivers an electromagnetic wave transmitted from the skin to the cochlea and comprises a coil, a magnet and electrodes that are configured to have different thickness. Preferably the electrodes are made of biocompatible platinum or platinum alloy.

The sound processing unit is attached on the skin at a temple of the user and is fixed to the internal receiving unit by magnetic attraction. It transforms the sound around the user into an electromagnetic energy and transmits it to the internal receiving unit. The sound processing unit comprises a microphone, a volume controller, a coil, a magnet and an electronic circuitry.

The power needed to operate the sound processing unit can be supplied from a battery pack or a charger. For example, a battery pack may be connected to the sound processing unit through a compact connector.

Unlike the conventional multi-channel cochlear implant, the cochlear implant according to the present invention enables a new and simple surgery with minimized adverse effects. The conventional cochlear implantation requires the formation of passage by removing bones for the insertion of electrodes by mastoidectomy. Such an operation takes approximately 3 hours and requires general anesthesia.

In contrast, since the cochlear implant according to the present invention has a small-sized internal receiving unit and the thickness of the electrode is different from area to area, it can be easily implanted, for example, by trans-canal surgery. Since the electrode of the cochlear implant according to the present invention can be inserted into a small space formed at between the skin and the bone, it can be easily implanted without mastoidectomy. The surgery can be completed in about 30 minutes or less. Further, the risk during the surgery can be minimized and the patients can do their regular activity quickly after the surgery.

Since the electrode is inserted into the small space between the skin and the bone, it needs to be elaborately designed. For this purpose, of the electrodes of the internal receiving unit, the single wire of the active electrode has different thickness in at least two, preferably three, regions. The electrode is inserted into the space formed at between the mastoid bone and the ear canal skin. The electrode wire passes through the eardrum of the middle ear and reaches to the spiral ganglion of the cochlea. Thus, the electrode needs not be inserted deep in the cochlea and the damage of the cochlea during the surgery can be minimized.

Advantageous Effects

The present invention provides a cochlear implant having simple construction with low cost. This cochlear implant enables a simple surgery and minimizes the risk of hair cell damage or infection caused by skin damage. And, the cochlear implant of the present invention can provide improved hearing ability without the need of long-lasting post-implantation therapy. The present invention is expected to improve hearing ability of the people suffered from hearing failures.

BRIEF DESCRIPTION OF THE DRAWINGS

FIG. 1 is a schematic view of the internal receiving unit of the conventional cochlear implant.

FIG. 2 is an exploded of the conventional cochlear implant at a region denoted as A in FIG. 1.

FIG. 3 is a schematic view of the internal receiving unit of the cochlear implant of the present invention.

FIG. 4 is a cross sectional view of the internal receiving unit of the cochlear implant of the present invention.

FIG. 5 is a perspective view of the sound processing unit of the cochlear implant of the present invention.

FIG. 6 is a cross-sectional view of the inside of the sound processing unit of the cochlear implant of the present invention.

FIG. 7 is a schematic view of the external power supply of the cochlear implant of the present invention.

FIG. 8 is a schematic view of the signal processing by the cochlear implant according to the present invention.

FIG. 9 is a flowchart illustrating an implantation procedure of the cochlear implant of the present invention.

FIG. 10 is a schematic view of the cochlear implant of the present invention after implantation.

MODE FOR THE INVENTION

Hereinafter, preferred embodiments of the present invention will be more fully illustrated referring to the accompanying drawings.

FIG. 3 is a schematic view of the internal receiving unit of the cochlear implant of the present invention. The internal receiving unit (100) comprises a receiving part (110), which wirelessly receives external signal, and an electrode part. The electrode part comprises an active electrode (120a) and a reference electrode (120b).

As illustrated in FIG. 4, the active electrode (120a) is made up of three regions with different thickness. The first region (I) is connected to the receiving part (110). The second region (II) has a smaller thickness than the first region (I) and the third region (III) has a smaller thickness than the second region (II). Alternatively, the second region may have the same thickness with the third region, if necessary. The first region (I) has the largest thickness and provides rigidity when the active electrode is inserted into the body. In contrast, the second region (II) and the third region (III) enable easy implantation of the active electrode (120a) into the small space between the mastoid bone and the skin, without grinding the bone. The first region is longest and the third region is shortest. The third region (III) serves as a contact point where the electrical stimulation is finally delivered to the cochlea.

Preferably, at least a part of each of the active electrode and the reference electrode, excluding ends of the electrodes, is coated with a biocompatible material (e.g., silicone or silicone compound). In this case, the thickness of the first region (I), the second region (II) and the third region (III) can be configured to have different thicknesses by controlling the thickness of the biocompatible coat. For example, the active electrode (120a) can be constructed with a wire having a suitable thickness and the first region may be coated with a biocompatible coat of a certain thickness, the second region with a smaller thickness, and the third region may be not coated.

The thickness of the second region (II) is smaller than 0.5 mm, preferably smaller than 0.3 mm. If the active electrode is constructed with gradually smaller thickness like this, the active electrode can be inserted into the space formed at between the mastoid bone and the skin. Further, the risk of the active electrode tearing the skin and being exposed outward, thereby resulting in infection, can be prevented.

Preferably, the first region (I) and the second region (II) are each independently approximately 25-35 mm long and the third region (III) is 5-7 mm long. As will be described below, the third region (III) is inserted into the scala tympani of the cochlea and directly delivers the electrical stimulation signal to the spiral ganglion.

The reference electrode (120b) is shorter than the active electrode and is inserted into the skin behind the ear. Contact points may be formed at the ends of the active electrode (120a) and the reference electrode (120b) without biocompatible coating.

The receiving part (110) comprises a coil (112) for receiving an stimulation signal from outside and a magnet (114) for non-contact fixation with the external unit, inside a case made of a biocompatible material (e.g., polyether ether ketone). The coil (112) can be made of, for example, copper wire.

The shape of the receiving part (110) is not particularly limited, but a round disk is preferable. In this case, the receiving part may have a diameter of smaller than 22 mm, preferably in the range from 10 to 18 mm. And, the receiving part may have a thickness of smaller than 4 mm, preferably in the range from 2 to 3 mm. Silicone may be filled inside the case of the receiving part.

FIG. 5 is a perspective view of the sound processing unit of the cochlear implant of the present invention, which is attached outside the body, and FIG. 6 is a cross-sectional view of the inside of the sound processing unit.

A volume controller (210) and a microphone (220) are equipped with at the surface of the round disk-shaped case (215) and a coil (240) for transmitting a signal, a magnet (260) for non-contact fixation with the internal receiving unit and a PCB-type electronic circuitry (250) are equipped within the case for the processing the analog sound.

The sound processing unit may be attached, for example, behind the ear or at the temple. Alternatively, it may be put on around the ear with aid of a supporting member.

The volume controller (210) controls the strength of the sound signal. The sound is input through the microphone (220). The electronic circuitry (250) transforms the sound signal into an electronic signal and, following an adequate modulation process, transmits the signal to the internal receiving unit through the transmission coil (240).

A jack (230) is equipped at one side of the case of the sound processing unit for electrical connection with an external power supply. FIG. 7 is a schematic view of the external power supply of the cochlear implant of the present invention. The external power supply (280) is a rechargeable battery and connected to the sound processing unit through a connector.

FIG. 8 is a schematic view of the signal processing by the cochlear implant according to the present invention.

The sound processing unit (200) and the internal receiving unit (100) are fixed by non-contact method with each other by the magnets (260, 114) and wirelessly transmit and receive the signal between them (I). The internal receiving unit (100) directly delivers the electrical stimulation to the cochlea (II). In particular, an important feature of the present invention is that central stimulation is provided from the internal receiving unit (100) through the spiral ganglion of the cochlea, whereas the conventional multi-channel cochlear implant is based on frequency-based multiple stimulation of the particular regions of the cochlea, A detailed description will be given later.

FIG. 9 is a flowchart illustrating an implantation procedure of the cochlear implant of the present invention.

A surgeon locally anesthetizes rear of the pinna and/or inside of the external auditory meatus, and cuts open the rear of the ear slightly apart from the pinna (S1). Then, the mastoid bone is separated from the ear canal skin (S2).

Subsequently, cochleastomy is performed at the front of the round window (S3). Although different from patient to patient, the cochleastomy is performed as deep as 3-5 mm in the cochlea. Next, the internal receiving unit is inserted, so that the end of the active electrode is inserted into the cochlea. The reference electrode of the internal receiving unit is positioned below the skin (S4). Suture is performed after the insertion of the internal receiving unit has been completed (S5).

This trans-canal surgery has advantages that the surgery can be performed simply under local anesthesia by inserting the electrode into the small space between the skin and the bone, and that the surgery can be completed in short time and the risk during the surgery can be minimized.

FIG. 10 is a schematic view of the cochlear implant of the present invention after implantation. The internal receiving unit (100) is implanted around the auditory canal (310) of the outer ear (300). The reference electrode (120b) of the internal receiving unit is inserted into the ear canal skin (330) neighboring the receiving part (110). In contrast, the active electrode (120a) is extended through the small space formed at between the ear canal skin (330) and the mastoid bone (320) to the cochlea (360), passing through the eardrum (340) of the middle ear (350). The end of the active electrode (120a) comes in contact with the spiral ganglion (365) of the cochlea (360).

Another distinguishing feature of the cochlear implant according to the present invention is that it directly stimulates the spiral ganglion at the center of the cochlea, not the dendrites of the hair cells, which tend to be easily damaged. Accordingly, the electrode needs not be inserted deep into the cochlea and the risk of damaging the hair cells during the surgery is fundamentally prevented and the surgery can be performed very easily. The transmission process of the electrical stimulation is simple sound from outside is transferred to the spiral ganglion by the cochlear implant and the auditory nerve is stimulated. Also, since the full-spectrum signal is directly transferred to the spiral ganglion, not by the frequency-based multiple electrical stimulation, improved tonal sensibility and sound recognition are attained.

As described, it should be evident that the present invention can be implemented through a variety of configurations in the aforementioned technical field without affecting, influencing or changing the spirit and scope of the present invention. Therefore, it is to be understood that the examples and applications illustrated herein are intended to be in the nature of description rather than of limitation. Furthermore, the meaning, scope and higher conceptual understandings of the present invention as well as modifications and variations that arise therefrom should be understood to be extensions to this invention.

The invention claimed is:

1. A cochlear implant for improving the hearing ability of a patient suffered from hearing impairment, comprising an internal receiving unit configured to be implanted into the body, which comprises a receiving part for receiving an external signal, an active electrode and a reference electrode extending from the internal receiving unit, characterized in that the active electrode is constructed with a single electrode wire having a single electrode contact point for conducting a single full-spectrum signal to a body's spiral ganglion, the wire having substantially different thicknesses in at least two different regions located along the length of the electrode wire, the two different regions being separated from one another by a stepped intermediate region therebetween, wherein the thicknesses change from one to the other, the wire electrode being characterized by a thickest wire electrode portion at a first end thereof extending from the receiving unit and a thinnest wire electrode portion at an opposite end thereof, the thinnest wire electrode portion configured for single-point contact with a defined region of the body's cochlea.

2. The cochlear implant as set forth in claim 1, wherein the active electrode has three regions with different thicknesses comprising a first region adjoining the receiving part, a second region having a thickness substantially smaller than the first region and a third region having a thickness substantially smaller than the second region.

3. The cochlear implant as set forth in claim 1, wherein the opposite end of the active electrode is configured to be inserted into the body's scala tympani of a cochlea, and wherein the opposite end is configured to directly stimulate the body's spiral ganglion.

4. The cochlear implant as set forth in claim 1, wherein the active electrode of the internal receiving unit is configured to be inserted into a space formed between the body's mastoid bone and the body's ear canal skin.

5. The cochlear implant as set forth in claim 1, wherein the active electrode of the internal receiving unit comprises a first region adjoining the receiving part, a second region being shorter than the first region and a third region being substantially shorter than the second region.

6. The cochlear implant as set forth in claim 1, wherein the reference electrode is shorter than the active electrode.

7. The cochlear implant as set forth in claim 1, wherein the receiving part comprises a coil for receiving an electrical stimulation signal from an external unit positioned outside the body, and wherein the receiving part further comprises a magnet for non-contact fixation with the external unit.

8. The cochlear implant as set forth in claim 1, wherein at least a part of each of the active and reference electrodes is coated with a biocompatible material.

9. The cochlear implant as set forth in claim 1, wherein the receiving part is protected by a biocompatible case containing a filler.

* * * * *